United States Patent
Rao et al.

(10) Patent No.: US 7,872,161 B2
(45) Date of Patent: Jan. 18, 2011

(54) PROCESS FOR PRODUCING 2,3,3,3-TETRAFLUOROPROPENE

(75) Inventors: Velliyur Nott Mallikarjuna Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 107 days.

(21) Appl. No.: 12/444,526

(22) PCT Filed: Nov. 15, 2007

(86) PCT No.: PCT/US2007/024061

§ 371 (c)(1),
(2), (4) Date: Apr. 6, 2009

(87) PCT Pub. No.: WO2008/060614

PCT Pub. Date: May 22, 2008

(65) Prior Publication Data

US 2010/0022808 A1    Jan. 28, 2010

Related U.S. Application Data

(60) Provisional application No. 60/859,174, filed on Nov. 15, 2006.

(51) Int. Cl.
C07C 17/10 (2006.01)
C07C 17/00 (2006.01)
C07C 17/26 (2006.01)

(52) U.S. Cl. .................. 570/176; 570/156; 570/257

(58) Field of Classification Search .......... 570/176, 570/156, 257
See application file for complete search history.

(56) References Cited

U.S. PATENT DOCUMENTS

| 5,629,461 A | 5/1997 | Yasuhara et al. |
| 6,031,141 A | 2/2000 | Mallikarjuna et al. |
| 6,958,424 B1 | 10/2005 | Nair et al. |
| 2006/0217577 A1 | 9/2006 | Mukhopadhyay et al. |
| 2007/0096053 A1 | 5/2007 | Nair et al. |

FOREIGN PATENT DOCUMENTS

| JP | 8-193039 | 7/1996 |
| WO | 9101287 | 2/1991 |
| WO | 2006094303 | 9/2006 |
| WO | 2007056128 | 5/2007 |
| WO | 2008030440 | 3/2008 |
| WO | 2008054778 | 5/2008 |
| WO | 2008054779 | 5/2008 |
| WO | 2008054780 | 5/2008 |
| WO | 2008060612 | 5/2008 |
| WO | 2008060616 | 5/2008 |

OTHER PUBLICATIONS

Haszeldine & Steele, Journal of Chemical Society, pp. 2193-2197 (1957).
Database Caplus [Online] Chemical Abstracts Service, Columbus, Ohio, US; Aoyama, Hiroichi et al: "Preparation of Hexafluoropropene" XP002484314 Retrieved From STN Database Accession No. 1996:571586 Abstract & JP 08 193039A (Daikin Ind Ltd, Japan) Jul. 30, 1996.

*Primary Examiner*—Jafar Parsa

(57) ABSTRACT

A process is disclosed for making $CF_3CF=CH_2$. The process involves (i) contacting $CHCl_2CF_2CF_3$ in a reaction zone in the presence of a catalytically effective amount of a dehydrofluorination catalyst to produce $CCl_2=CFCF_3$; (ii) contacting $CCl_2=CFCF_3$ with $H_2$ formed in (i) in a reaction zone in the presence of a catalyst comprising a catalytically effective amount of palladium supported on a support selected from the group consisting of alumina fluorided alumina, aluminum fluoride and mixtures thereof, to produce a product mixture comprising $CF_3CF=CH_2$, wherein the mole ratio of $H_2$ to $CCl_2=CFCF_3$ fed to the reaction zone is between about 1:1 and about 4:1 and (iii) recovering $CF_3CF=CH_2$ from the product mixture formed in (ii).

2 Claims, No Drawings

PROCESS FOR PRODUCING 2,3,3,3-TETRAFLUOROPROPENE

FIELD OF THE INVENTION

The present invention relates to processes that involve the production of halogenated hydrocarbon products comprising 2,3,3,3-tetrafluoropropene.

BACKGROUND OF THE INVENTION

As a result of the Montreal Protocol phasing-out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a ($CF_3CH_2F$) being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is considerable interest in developing new refrigerants with reduced global warming potential, as well as zero ozone depletion potential, for the mobile air-conditioning market, and in other refrigeration applications.

2,3,3,3-Tetrafluoropropene ($CH_2=CFCF_3$, HFC-1234yf) has been identified as a potential component in refrigerant blends (see PCT application published as WO 2006/094303). HFC-1234yf has been prepared by reaction of $CH_2ClC_2F_5$ with zinc in ethanol as reported by Haszeldine and Steele in Journal of the Chemical Society, pages 2193-2197 (1957) or as a by product in the vapor phase fluorination of 3-chloro-1,1,2,2-tetrafluoropropane over chromium catalysts as disclosed by Yasuhara, et. al. in U.S. Pat. No. 5,629,461.

There is a need for new manufacturing processes for the production of HFC-1234yf.

SUMMARY OF THE INVENTION

The present invention provides a process for making $CF_3CF=CH_2$ (HFC-1234yf). The process comprises (i) contacting $CHCl_2CF_2CF_3$ (HCFC-225ca) in a reaction zone in the presence of a catalytically effective amount of a dehydrofluorination catalyst to produce $CCl_2=CFCF_3$ (CFC-1214ya); (ii) contacting $CCl_2=CFCF_3$ (CFC-1214ya) formed in (i) with hydrogen ($H_2$) in a reaction zone in the presence of a catalyst comprising a catalytically effective amount of palladium supported on a support selected from the group consisting of alumina, fluorided alumina, aluminum fluoride and mixtures thereof, to produce a product mixture comprising $CF_3CF=CH_2$ (HFC-1234yf), wherein the mole ratio of $H_2$ to $CCl_2=CFCF_3$ (CFC-1214ya) fed to the reaction zone is between about 1:1 and about 4.1 and; (iii) recovering $CF_3CF=CH_2$ (HFC-1234yf) from the product mixture formed in (ii).

DETAILED DESCRIPTION

The present invention provides a process for making HFC 1234yf employing a multi-step process.

In the first step of the process, HCFC-225ca is dehydrofluorinated over a suitable catalyst for a time sufficient to convert at least a portion of HCFC-225ca to CFC-1214ya.

HCFC-225ca may be prepared by reacting $CCl_3CF_2CF_3$ (CFC-215cb) with hydrogen as disclosed by Baker in U.S. Pat. No. 5,300,712. CFC-215cb can be prepared by the reaction of fluorotrichloromethane ($CCl_3F$) with tetrafluoroethylene ($CF_2=CF_2$) in the presence of an aluminum halide as disclosed in U.S. Patent Application No. 60/855,541, filed Oct. 31, 2006, which is herein incorporated by reference in its entirety (see also PCT/US2007/22993, filed Oct. 31, 2007). In particular, HCFC-225ca can be produced by reacting $CCl_3F$ with $CF_2=CF_2$ in a reaction zone in the presence of a catalytically effective amount of composition having a bulk formula of $AlCl_xBr_yF_{3-x-y}$ wherein the average value of x is 0 to 3, the average value of y is 0 to 3-x, provided that the average values of x and y are not both 0, to produce the CFC-215cb; and partially hydrogenating the CFC-215cb to HCFC-225ca.

The dehydrofluorination reaction may be conducted in the vapor phase in a reaction zone containing the dehydrofluorination catalyst at temperatures of from about 200° C. to about 500° C. and preferably from about 300° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of HCFC-225ca can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to HCFC-225ca is from about 5:1 to 1:1. Nitrogen is the preferred inert gas.

Typical dehydrofluorination reaction conditions and dehydrofluorination catalysts are disclosed in U.S. Pat. No. 5,396,000, which is incorporated herein by reference in its entirety. Preferably, the dehydrofluorination catalyst comprises at least one catalyst selected from the group consisting of carbon, aluminum fluoride, fluorided alumina, trivalent chromium oxide, and trivalent chromium chloride, fluoride, or chlorofluoride preferably supported on a support such as carbon, aluminum fluoride, or fluorided-alumina.

Other dehydrofluorination catalysts useful for converting HCFC-225ca to CFC-1214ya are described in U.S. Pat. No. 6,093,859 and U.S. Pat. No. 6,369,284; the teachings of these disclosures are incorporated herein by reference.

The effluent form the dehydrofluorination reactor typically includes HF, CFC-1214ya, some CFC-1215yb and $CF_3CHFCCl_2F$ (HCFC-225eb), and any unconverted HCFC-225ca.

The CFC-1214ya may be separated from the product mixture formed in the dehydrofluorination reactor by methods known to the art. Since HF is present in the effluent, if desired, this separation can also include, isolation of azeotrope or near azeotrope composition of CFC-1214ya and HF. HF-free CFC-1214ya may be obtained using procedures similar to those disclosed in U.S. Patent Application Publication No. 2006/0106263 which is hereby incorporated herein by reference. Unreacted HCFC-225ca can be recycled back to the dehydrofluorination reactor.

In the second step of the process, CFC-1214ya is hydrogenated over a suitable catalyst.

Catalysts suitable for carrying out the process of making HFC-1234yf from CFC-1214ya in accordance with this invention comprise palladium and may optionally comprise additional Group VIII metals (e.g., Pt, Ru, Rh or Ni). The palladium is supported on alumina, fluorided alumina, aluminum fluoride or a mixture thereof. The palladium-containing precursor used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride or rhodium nitrate) as described by Satterfield on page 95 of Heterogenous Catalysis in Industrial Practice, $2^{nd}$ edition (McGraw-Hill, New York, 1991). Palladium supported on alumina is available commercially. A suitable procedure for preparing a catalyst-containing palladium on fluorided alumina is described in U.S. Pat. No. 4,873,381, which is incorporated herein by reference.

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight-based on the weight of the total metals present on the support.

The relative amount of hydrogen fed during contact of CFC-1214ya in a reaction zone containing the palladium-containing catalyst is from about 1 mole of $H_2$ per mole of CFC-1214ya to about 4 moles of $H_2$ per mole of CFC-1214ya, preferably from about 1 mole of $H_2$ per mole of CFC-1214ya to about 3 moles of $H_2$ per mole of CFC-1214ya and more preferably from about 1 mole of $H_2$ per mole of CFC-1214ya to about 2 moles $H_2$ per mole of CFC-1214ya.

The reaction zone temperature for the catalytic hydrogenation of CFC-1214ya is typically in the range of from about 100° C. to about 400° C., and preferably is in the range of from about 125° C. to about 350° C. The contact time is typically in the range of from about 1 to about 450 seconds, and preferably is in the range of from about 10 to about 120 seconds. The reactions are typically conducted at near atmospheric pressure.

The effluent from the reaction zone typically includes HCl, unreacted hydrogen, $CF_3CF=CH_2$, higher boiling products and intermediates typically including one or more of $CF_3CF=CHCl$ (HCFC-1224yd), $CF_3CHFCH_2Cl$ (HCFC-244eb), $CF_3CHFCH_3$ (HFC-254eb), and any unconverted CFC-1214ya.

The desired HFC-1234yf is separated by methods known to the art. The unreacted CFC-1214ya and HCFC-1224yd, the product of intermediate hydrogenation, can be recycled back to the hydrogenation reactor The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

EXAMPLES

The processes of the present invention are demonstrated by the following prophetic examples.

Example 1

Dehydrofluorination of HCFC-225ca ($CHCl_2C_2F_5$)

An Inconel™ tube (⅝ inch OD (159 cm)) is charged with a commercial sample of 25 weight percent chromium(III) chloride supported on carbon (10 cc, 3.4 g, 12-20 mesh (1.68-0.84 mm)). The tube is connected to a reactor system and surrounded with an electrically-heated furnace. The catalyst is then activated by purging with nitrogen (37.5 sccm, $6.2 \times 10^{-7}$ m³/s) at 300° C. for 2 hours. The catalyst is then fluorinated with a 3:1 mixture of nitrogen and hydrogen fluoride (total flow 35 sccm, $5.8 \times 10^{-7}$ m³/s) as the temperature in the reactor is increased from 300° C. to 425° C. over the course of 9 hours. The ratio of nitrogen to hydrogen fluoride is then changed from 3:1 to 0:4 with a total flow rate of 35 sccm ($5.8 \times 10^{-7}$ m³/s) over the course of 3 hours at 425° C. The flow of HF is then stopped and the reactor tube cooled to about 350° C. under a nitrogen flow.

A mixture of HCFC-225ca and nitrogen (molar ratio 1:3) is then passed through the catalyst bed at 350° C. with a contact time of about 30 seconds. The pressure in the reactor is nominally atmospheric. Analysis of the reactor effluent shows at least 50% or the HCFC-225ca is converted with CFC-1214ya being the major reaction product. The effluent also contains unreacted starting material and lesser amounts of $C_3HCl_3F_4$ and $C_3HClF_6$ isomers.

Example 2

Hydrodechlorination of CFC-1214ya ($CF_3CF=CCl_2$)

A commercial palladium on aluminum oxide catalyst (0.5% Pd/$Al_2O_3$, 10 cc, 14.45 g, 12-20 mesh (1.68-0.84 mm)) is placed in a 30.5 cm×1.27 cm o.d. Heastelloy® tube. The tube is connected to a reactor system and surrounded with an electrically-heated furnace. The catalyst is dried for three hours under a nitrogen purge (25 sccm, $4.2 \times 10^{-7}$ m³/s) as the temperature of the furnace is raised to 30° C. The reactor is allowed to cool to 150° C., and then hydrogen gas (20 sccm, $3.3 \times 10^{-7}$ m³/s) is passed into the reactor for three hours as the temperature in the reactor is increased to 300° C. The reactor is cooled again to 150° C. under a flow of nitrogen (20 sccm, $3.3 \times 10^{-7}$ m³/s). The catalyst is then fluorinated with mixture of nitrogen and hydrogen fluoride according to following sequence (time in hours, flow rate nitrogen, flow rate HF, temperature):

2 h, $7.5 \times 10^{-7}$ m³/s, $8.3 \times 10^{-8}$ m³/s, 150° C.; 2 h, $6.6 \times 10^{-7}$ m³/s, $1.7 \times 10^{-7}$ m³/s, 150° C.; 2 h, $6.6 \times 10^{-7}$ m³/s, $1.7 \times 10^{-7}$ m³/s, 200° C.; 2 h, $6.6 \times 10^{-7}$ m³/s, $1.7 \times 10^{-7}$ m³/s, 250° C.; 2 h, $4.2 \times 10^{-7}$ m³/s, $4.2 \times 10^{-7}$ m³/s, 250° C. The flow of hydrogen fluoride is then stopped and the reactor is purged with nitrogen.

A mixture of hydrogen and $CF_3CF=CCl_2$(CFC; 1214ya) and nitrogen in a 2:1:2 molar ratio is then fed to the catalyst at 200° C. with a contact time of 30 seconds. The pressure in the reactor is nominally atmospheric. Under these conditions, at least 50% of the CFC-1214ya is converted with $CF_3CF=CH_2$ being the major reaction product. The effluent also contains unreacted starting material and lesser amounts of $E/Z-CF_3CF=CHCl$ and $CF_3CHFCH_3$.

What is claimed is:

1. A process for making $CF_3CF=CH_2$ comprising:
   (i) contacting $CHCl_2CF_2CF_3$ in a reaction zone in the presence of a catalytically effective amount of a dehydrofluorination catalyst to produce $CCl_2=CFCF_3$;
   (ii) contacting $CCl_2=CFCF_3$ formed in (i) with $H_2$ in a reaction zone in the presence of a catalyst comprising a catalytically effective amount of palladium supported on a support selected from the group consisting of alumina, fluorided alumina, aluminum fluoride and mixtures thereof, to produce a product mixture comprising $CF_3CF=CH_2$, wherein the mole ratio of $H_2$ to $CCl_2=CFCF_3$ fed to the reaction zone is between about 1:1 and about 4:1 and; (iii) recovering $CF_3CF=CH_2$ from the product mixture formed in (ii).

2. The process of claim 1 wherein the $CHCl_2CF_2CF_3$ dehydrofluorinated in (i) is produced by reacting $CCl_3F$ with $CF_2=CF_2$ in a reaction zone in the presence of a catalytically effective amount of composition having a bulk formula of $AlCl_xBr_yF_{3-x-y}$ wherein the average value of x is 0 to 3, the average value of y is 0 to 3−x, provided that the average values of x and y are not both 0, to produce the $CCl_3CF_2CF_3$; and partially hydrogenating the $CCl_3CF_2CF_3$ to $CHCl_2CF_2CF_3$.

* * * * *